United States Patent [19]

George et al.

[11] Patent Number: 5,096,900
[45] Date of Patent: Mar. 17, 1992

[54] (4-PIPERIDYL)METHYL)2,3-DIHYDRO-1H-ISOINDOLE AND -2,3,4,5-TETRAHYDRO-1H-BENZAZEPINE DERIVATIVES, THEIR PREPARATION AND THEIR APPLICATION IN THERAPY

[75] Inventors: Pascal George, St. Arnoult en Yvelines; Mireille Sevrin, Paris; Michel Mangane, Chatillon s/Bagneux, all of France

[73] Assignee: Synthelabo, Paris, France

[21] Appl. No.: 503,941

[22] Filed: Feb. 8, 1990

Related U.S. Application Data

[62] Division of Ser. No. 377,929, Jul. 11, 1989.

[30] Foreign Application Priority Data

Jul. 12, 1988 [FR] France .................. 88 09450

[51] Int. Cl.$^5$ .................. C07D 223/16; A61K 31/55
[52] U.S. Cl. .................. 514/213; 540/593; 540/594
[58] Field of Search .................. 514/213; 540/593, 594

[56] References Cited

U.S. PATENT DOCUMENTS 4,435,410  3/1984  Le Furi et al. .................. 546/201

FOREIGN PATENT DOCUMENTS 3541811  6/1987  Fed. Rep. of Germany ...... 540/594
868933  11/1986  South Africa .
1140049  1/1969  United Kingdom .......... 540/593

OTHER PUBLICATIONS

Organic Syntheses, vol. 5, 1976, pp. 406 to 408 and 1064 to 1066.

Ruggli et al., Helvetica Chemica Acta, vol. 29, 1935, pp. 1388 to 1395.
Deady et al., JCS, Perkins I, 1973, pp. 782 to 783.

*Primary Examiner*—Mukund J. Shah
*Assistant Examiner*—E. C. Ward
*Attorney, Agent, or Firm*—Fleit, Jacobson, Cohn, Price, Holman & Stern

[57] ABSTRACT

A benzazepine derivative which is a compound of formula (I):

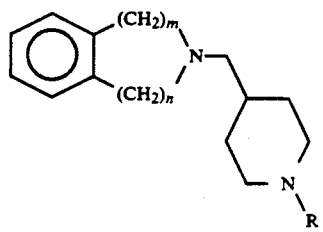

in which:
each of m and n denotes the number 1, or
each of m and n denoted the number 2, or
m denotes the number 3 and n denoted the number 1; and
R denotes hydrogen or a group of formula —Z—R' in which Z denotes a —CO— or —CH$_2$— group and R' denotes a phenyl group which is unsubstituted or substituted with from one to three substituents selected from halogen atoms, linear or branch (C$_1$-C$_3$) groups and linear or branched (C$_1$-C$_3$) alkoxy groups,
or a pharmacologically acceptable acid addition salt.

6 Claims, No Drawings

[54] (4-PIPERIDYL)METHYL)2,3-DIHYDRO-1H-DOLE AND -2,3,4,5-TETRAHYDRO-1H-BENZAZEPINE DERIVATIVES, THEIR PREPARATION AND THEIR APPLICATION IN THERAPY

This is a divisional of application Ser. No. 377,929 filed July 11, 1989.

The present application relates to [(4-piperidyl)-methyl]-2,3-dihydro-1H-isoindole and -2,3,4,5-tetrahydro-1H-benzazepine derivatives, to their preparation and to their application in therapy.

The present invention provides a benzazepine derivative which is a compound of formula (I):
in which:
each of m and n denotes the number 1, or
each of m and n denotes the number 2, or
m denotes the number 3 and n denotes the number 1; and R deontes hydrogen or a group of formula —Z—R' in which Z denotes a —CO— or —CH$_2$— group and R' denotes a phenyl group which is unsubstituted or substituted with from one to three substituents selected from halogen atoms, linear or branched (C$_1$-C$_3$) alkyl groups and linear or branched (C$_1$-C$_3$) alkoxy groups.
or a pharmacologically acceptable acid addition salt thereof. R', when substituted, is preferably substituted in the 3-position. Suitable substituents are chlorine atoms, methyl groups and ethoxy groups. The preferred salts are dihydrochloride, hydrochloride, difumarate and fumarate salts.

The present invention also provides a process for preparing a derivative as defined above, in which R denotes a group of formula —Z—R' in which Z denotes a —CO— group, wherein a compound of formula (II):

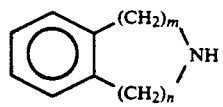

in which m and n are as defined above, is reacted with a tosylate of formula (III):

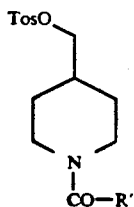

in which Tos denotes a tosyl group and R' is as defined above, at a temperature of 20° to 150° C., and the compound of formula (I) thus obtained is, if desired, converted to a pharmacologically acceptable acid addition salt thereof.

The present invention also provides a process for preparing a derivative as defined above, in which R denotes a group of formula —Z—R' in which Z denotes a —CH$_2$— group, wherein a compound of formula (I) in which R denotes a group of formula —Z—R' in which Z denotes a —CO— group is reduced with a simple or complex hydride of boron or aluminium in an ethereal solvent at a temperature of from 20° to 100° C., and the compound of formula (I) thus obtained is, if desired, converted to a pharmacologically acceptable acid addition salt thereof.

Scheme 1 below illustrates how the compounds of formula (I) may be prepared.

The compound of formula (I) in which Z denotes a —CO— group is prepared first, by reacting a compound of formula (II) with a tosylate of formula (III), either in the absence or presence of an inert solvent such as dimethylformamide, toluene or xylene, at a temperature of 20° to 150° C., and optionally in the presence of an organic base such as a tertiary amine or an inorganic base such as an alkali metal carbonate or hydrogen carbonate.

A compound of formula (Ia) which corresponds to formula (I) when Z denotes a —CO— group is thereby obtained.

If it is desired to prepare a compound of formula (I) in which Z denotes a —CH$_2$— group, the compound of formula (Ia) is reduced with a simple or complex hydride of boron or aluminium, for example lithium aluminium hydride, aluminium hydride, the diborane/tetrahydrofuran complex or the diborane/methyl sulphide complex, or any equivalent means, in an ethereal solvent such as diethyl ether, tetrahydrofuran or dioxane, at a temperature of from 20° to 100° C.

Scheme 1

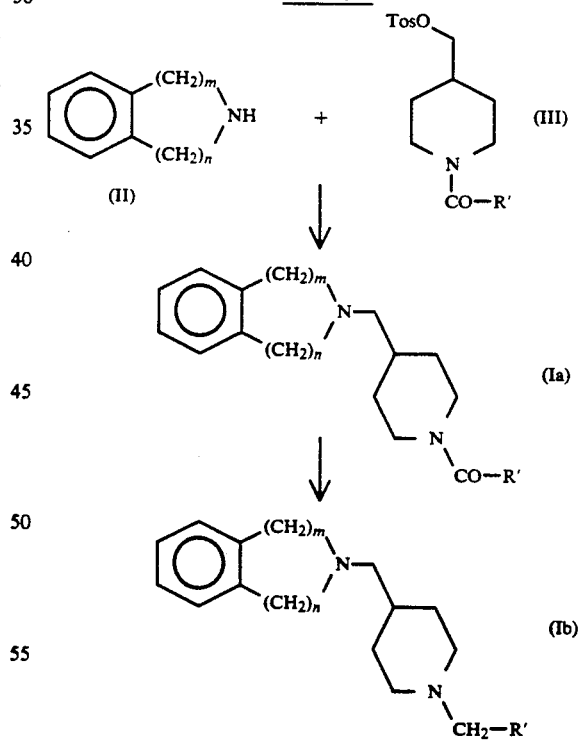

The compound of formula (Ib), which corresponds to formula (I) when Z denotes a —CH$_2$— group, is thereby obtained.

Finally, the compounds of formula (I) in which R denotes hydrogen may be obtained by debenzylation of the compounds of formula (I) in which R denotes a benzyl group, for example by hydrogenolysis with gaseous hydrogen under a pressure of 0.1 to 0.5 MPa in the presence of a metal catalyst, optionally on an inert or basic support, for example palladium on charcoal, barium sulphate or calcium carbonate, in an alcoholic solvent, for example methanol or ethanol, at a temperature of 20° to 80° C.

Therefore the present invention also provides a process for preparing a derivative as defined above in which R denotes hydrogen, wherein a compound of formula (I) as defined above in which Z denotes a —CH$_2$— group is debenzylated, and the compound of formula (I) thus obtained is, if desired, converted to a pharmacologically acceptable acid addition salt thereof.

2,3-Dihydro-1H-isoindole of formula (II (m=n=1) may be obtained by a process such as that described in Organic Syntheses, Collective Vol. V, 406–408 and 1064–1066.

2,3,4,5-Tetrahydro-1H-3-benzazepine of general formula (II) (m=n=2) may be obtained by a process such as that described in Helvetica Chim. Acta, 18, 1388, (1935).

2,3,4,5-Tetrahydro-1H-2-benzazepine of general formula (II) (m=3 and n=1) may be obtained by a process such as that described in J. C. S., Perkin I, 782 (1973).

The tosylates of general formula (III) may be prepared according to a method illustrated in Scheme 2 below.

4-Piperidinemethanol of formula (IV) is reacted with an acid chloride of formula R'COCl, in which R' is as defined above, in an inert solvent such as a chlorinated solvent, at a temperature of from 20° to 80° C. An ester-amide of formula (V) is thereby obtained, which is saponified, for example with sodium or potassium hydroxide in a lower aliphatic alcoholic solvent, preferably ethanol, to obtain the alcohol of formula (VI), the tosylate of which is finally prepared by reaction thereof with tosyl chloride in a basic medium such as pyridine.

4-Piperidinemethanol of formula (IV) may be obtained, for example, by reduction of ethyl 4-piperidinecarboxylate with lithium aluminium hydride, or alternatively by reduction of ethyl 1-benzyl-4-piperidinecarboxylate in this manner followed by catalytic hydrogenolysis under pressure.

Finally, another variant of process, the detail of which is illustrated in Example 3 below, enables the compounds of the invention to be prepared from appropriately chosen 1,2-bis(bromoalkyl)benzenes and 1-phenylmethyl-4-piperidinecarboxamides or 4-piperidinemethanamines, with the formation of the nitrogen-containing ring of 2,3-dihydro-1H-indole or of the 2,3,4,5-tetrahydro-1H-benzazepines.

The Examples which follow illustrate in detail the preparation of a few compounds according to the invention. The elemental microanalyses and the IR and NMR spectra confirm the structures of the products obtained.

The numbers shown in brackets in the titles of the Examples correspond to those in the table given later.

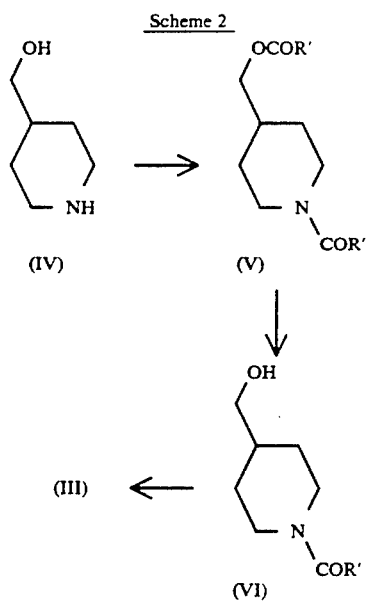

EXAMPLE 1

Compound No. 6

2-[{1-[(3-Methylphenyl)carbonyl]-4-piperidyl}methyl]-2,3-dihydro-1H-isoindole hydrochloride 1.1. 4-Piperidinemethanol 28.5 g (0.75 mol) of lithium aluminium hydride and 1.2 l of tetrahydrofuran are introduced into a 4-l three-necked round-bottomed flask equipped with a mechanical stirring system and a condenser. 117.9 g (0.75 mol) of ethyl 4-piperidinecarboxylate, dissolved in 1.2 l of tetrahydrofuran, are added to the suspension obtained, and the mixture is stirred for 6 h at 20° C. It is cooled to 0° C. and then hydrolyzed by adding successively 22 ml of water, 22 ml of 1 N sodium hydroxide and 46 ml of water. The mixture is stirred for 30 min at 20° C. and filtered, and the precipitate is washed with tetrahydrofuran and then with ether. The solvents are evaporated off under reduced pressure, and 84.4 g of an oil are obtained, this oil being used without further treatment in the next stage.

1.2 {1-[(3-Methylphenyl)carbonyl]-4-piperidyl} methyl 3-methylbenzoate 42.25 g (0.367 mol) of 4-piperidinemethanol and 430 ml of 1,2-dichloroethane are introduced under an argon atmosphere into a 3-l three-necked round-bottomed flask, and 82 g (0.81 mol) of triethylamine and then 125.2 g (0.81 mol) of 3-methylbenzoyl chloride are added. The mixture is heated under reflux for 4 h 30 min, a further 8.2 g (0.08 mol) of triethylamine and 12.5 g (0.08 mol) of 3-methylbenzoyl chloride are added and the mixture is heated for a further h.

The mixture is filtered, the salts are washed with 2-dichloroethane, the filtrate is evaporated under reduced pressure, the residue is dissolved in ethyl acetate, the solution is washed with saturated aqueous sodium chloride solution, the solvent is evaporated off under reduced pressure and the residue is recrystallized in a 1:1 isopropyl alcohol/ethyl acetate mixture. 80 g of a white solid are obtained Melting point: 80°–83° C.

1.3 1-[(3-Methylphenyl)carbonyl]-4-piperidinemethanol

A solution of 12.76 g (0.23 mol) of potassium hydroxide in 75 ml of ethanol and 75 ml of water is added to a solution of 80 g (0.23 mol) of {1-[(3-methylphenyl)carbonyl]-4-piperidyl}methyl 3-methylbenzoate in 400 ml of ethanol. The mixture is stirred at 20° C. for 3 h, the ethanol is evaporated off under reduced pressure and the aqueous phase is extracted with ethyl acetate. The organic phase is washed with water and then with saturated aqueous sodium chloride solution and dried ove magnesium sulphate. The solvent is evaporated off under reduced pressure, and 53 g of alcohol are obtained, this alcohol being used without further treatment in the next stage. 1.4. {1-[(3-Methylphenyl)carbonyl]-4-piperidyl}methyl (4-methylphenyl)sulphonate 53.3 g (0.28 mol) of 4-methylphenylsulphonyl chloride in 60 ml of pyridine are added to a solution of 52 g (0.22 mol) of 1-[(3-methylphenyl)carbonyl]-4-piperidinemethanol in 100 ml of pyridine. The mixture is stirred at 20° C. for 4 h and then poured into ice. The phase is extracted with dichloromethane and the organic phase is washed with 10N aqueous hydrochloric acid solution and dried over magnesium sulphate. The solvents are evaporated off under reduced pressure and 70 g of white solid are obtained. Melting point: 68°-70° C.

1.5. 2-[{1-(3-Methylphenyl)carbonyl]-4-piperidyl}methyl]-2,3-dihydro-1H-isoindole hydrochloride
3.6

3.6 g (0.03 mol) of 2,3-dihydro-1H-isoindole and 12.8 g (0.033 mol) of {1-[(3-methylphenyl)carbonyl]-4-piperidyl}methyl (4-methylphenyl)sulphonate are introduced into a 250 ml round-bottomed flask placed under an argon atmosphere, and the mixture is heated to 150° C. for 3 h 30 min. A thick brown oil is obtained, and this is diluted with dichloromethane, concentrated ammonia solution is added, the organic phase is separated, washed with water and dried over magnesium sulphate, the solvents are evaporated off under reduced pressure and the residue is purified by chromatography on a silica column. 7.5 g of base are isolated. Melting point: 125°-127° C.

The hydrochloride thereof is prepared by means of hydrochloric acid in 2-propanol, and recrystallized in an ethyl acetate/2-propanol mixture. Melting point: 217.5°-220° C.

EXAMPLE 2

Compound No. 7

2-[{1-[(3-Methylphenyl)methyl]-4-piperidyl}methyl]-2,3-dihydro-1H-isoindole difumarate 0.54 g (14.4 mmol) of lithium aluminium hydride in 20 ml of tetrahydrofuran is introduced into a 250-ml three-necked round-bottomed flask placed under an argon atmosphere, 3.15 g (9.42 mmol) of 2-[{1-[(3-methylphenyl)carbonyl]-4- piperidyl}methyl]-2,3-dihydro-1H-isoindole, dissolved in 75 ml of tetrahydrofuran cooled to 0° C., are added, and the mixture is stirred in the cold state for 5 min and then heated under reflux for 1 h. A clear orange solution is obtained, to which 7 ml of 6.5% strength sodium hydroxide is added while the solution is cooled. A dark orange suspension is obtained, and this is filtered, the filtrate is dried over magnesium sulphate, the solvent is evaporated off under reduced pressure and the residue is purified by chromatography on a silica column, eluting with a 96:4 dichloromethane/methanol mixture. 2.35 g of a brown oil, which crystallizes, are isolated. Melting point: 93.5-95° C.

This base (7.33 mmol) is dissolved in 150 ml of ethanol, a solution of 1.7 g (14.7 mmol) of fumaric acid in 100 ml of ethanol is added, the mixture is concentrated to half its initial volume, and the white solid which crystallizes is separated by filtration and recrystallized in a 1:1 ethyl acetate/ethanol mixture. 2.8 g of pure difumarate are finally obtained. Melting point 198°-200.5° C.

EXAMPLE 3

Compound No. 3

2-{[1-(Phenylmethyl)-4-piperidyl]methyl}-2,3-dihydro-1H-isoindole dihydrochloride A. First variant 3.A.1. 1-(phenylmethyl)-4-piperidinecarboxamide 123.0 g (0.96 mol) of 4-piperidinecarboxamide and 90.8 g (1.08 mol) of sodium bicarbonate are introduced under an argon atmosphere into 2 l of dry toluene. 180.6 g, equivalent to 125.6 ml (1.056 mol), of bromomethylbenzene are added, and the mixture is heated under reflux for 5 h.

The mixture is filtered hot. As the filtrate cools, a white precipitate forms. It is isolated and dried, and 113.4 g of dry product are obtained. Melting point: 160°-162° C.

3. A.2 2-{[1-(Phenylmethyl)-4-piperidyl]carbonyl-2,3-dihydro-1H-isoindole hydrochloride 2.3 g of 50% strength sodium hydride in oil (48.1 mmol), washed beforehand with petroleum ether, are introduced under an argon atmosphere into a round-bottomed flask, followed by 100 ml of dimethylformamide and then a solution of 5 g (22.9 mmol) of 1-(phenylmethyl)-4-piperidinecarboxamide in 45 ml of dimethylformamide, at room temperature and over a period of 20 min. The suspension is stirred for 1 h at room temperature and then 1 h at 60° C.

A solution of 6.05 g (22.9 mmol) of 1,2-bis(bromomethyl)benzene in 40 ml of dimethylformamide is then added in such a way as to maintain the temperature at between 60° and 70° C., and the mixture is stirred for 3 h at room temperature.

The mixture is poured into a mixture of ice and water and treated with ethyl acetate, the organic phase is separated, washed with water and dried and the solvent is evaporated off. An orange solid is obtained, and this is recrystallized in cyclohexane, washed with ether and recrystallized once more in cyclohexane. 1.1 g of white solid are obtained.

The latter is introduced into a mixture of 50 ml of isopropyl alcohol and 34.3 ml of a 0.1 N solution of hydrochloric acid in isopropyl alcohol, and the solution is heated under reflux and allowed to cool. 1.2 g of hydrochloride are obtained. Melting point: 243°-246° C. (decomposition).

3.A.3. 2-{[1-(Phenylmethyl)-4-piperidyl]methyl}-2,3-dihydro-1H-isoindole dihydrochloride A solution of 10.0 g (31.2 mmol) of 2-{[1-(phenylmethyl)-4-piperidyl]carbonyl}-2,3-dihydro-1H-isoindole in 20 ml of dry ether is added slowly in the cold state to 1.85 g (48.4 mmol) of lithium aluminium hydride in 300 ml of dry ether. The mixture is stirred for 30 min at room temperature and then for 7 h under reflux. It is then hydrolyzed with 8 ml of water and filtered, rinsing the solid with ether, and the filtrate is dried and concentrated. A yellow oil, which crystallizes rapidly, is obtained. It is taken up with ethanol and a stream of gaseous hydrochloric acid is passed into the solution. A cream-coloured solid is obtained, and this is recrystallized twice in a 2:1 ethanol/methanol mixture. 7.7 g of dihydrochloride are obtained. Melting point: 291°-293° C.

B. Second variant

3.B.1. 1-(Phenylmethyl)-4-piperidinemethanamine hydrochloride 50.0 g (229 mmol) of 1-(phenylmethyl)-4-piperidinecarboxamide and 13.0 g (343 mmol) of lithium aluminium hydride are introduced under an argon atmosphere into 2.5 l of dry ether, and the mixture is heated under reflux for 8 h. 50 ml of water are added, the mixture is filtered, rinsing the solid with ether, the organic phase is separated and dried and the solvent is evaporated off. 40.7 g of a yellow oil are obtained, and this is dissolved in 1.99 l of a 0.1 N solution of hydrochloric acid in isopropyl alcohol. The solution is concentrated to ⅔ of its volume and allowed to cool, and the white solid which has precipitated is filtered off and recrystallized in isopropyl alcohol. 33.7 g of hydrochloride are obtained. Melting point: 188°-190° C.

3.B.2. 2-{[1-(Phenylmethyl)-4-piperidyl]methyl}-2,3-dihydro-1H-isoindole dihydrochloride 1.97 g (7.48 mmol) of 1,2-bis(bromomethyl)benzene and 5.2 g (3.74 mmol) of potassium carbonate are introduced under an argon atmosphere into 40 ml of dimethylformamide. The mixture is cooled in an ice bath and 1.8 g of 1-(phenylmethyl)-4-piperidinemethanamine hydrochloride are added slowly.

The mixture is stirred for 4 h at room temperature and then poured into a mixture of water and ice. The solid is extracted with ethyl acetate, the organic phase is separated, washed with water and dried and the solvent is evaporated off. 1.8 g of a yellow oil are obtained, and this crystallizes and is dissolved in the heated state in 59 ml of a 0.1N solution of hydrochloric acid in isopropyl alcohol. The solution is allowed to cool, the white solid which has precipitated is filtered off and 0.8 g of dihydrochloride is isolated. Melting point: 291°-291.5° C.

EXAMPLE 4

Compound No. 1

2-[(4-Piperidyl)methyl]-2,3-dihydro-1H-isoindole dihydrochloride 56.6 g (149 mmol) of 2-{[1-(phenylmethyl)-4-piperidyl]methyl}-2,3-dihydro-1H-isoindole dihydrochloride, 300 ml of ethanol, 50 ml of water and 5 g of palladinized charcoal (10% palladium) are introduced into a Parr apparatus and a hydrogenolysis is performed under approximately 0.41 MPa for 9 h.

The mixture obtained is filtered, the filtrate is evaporated and the residue is taken up with a 1:1 methanol/ethanol mixture in the presenc of activated charcoal. The mixture is filtered, the filtrate is evaporated and 39.6 g of slightly bluish white dihydrochloride are obtained. Melting point: 298°-301° C.

EXAMPLE 5

Compound No. 14

2-[{1-[(3-Methylphenyl)carbonyl]-4-piperidyl}methyl]-2,3,4,5-tetrahydro-1H-3-benzazepine fumarate 3 g (0.02 mol) of 2,3,4,5-tetrahydro-1H-3-benzazepine, 7.6 g (0.02 mol) of {1-[(3-methylphenyl)carbonyl]-4-piperidyl}methyl 4-methylbenzenesulphonate, 2.8 g (0.02 mol) of potassium carbonate and 20 ml of dimethylformamide are introduced into a round-bottomed flask placed under argon and equipped with a stirring system. The mixture is stirred for 9 h at 90° C., cooled and poured into water. The mixture is extracted with dichloromethane, the organic phase is washed with water and dried over magnesium sulphate and the solvents are evaporated off under reduced pressure. 7.5 g of residue are obtained, and this is purified by chromatography on a silica column, eluting with ether, yielding 2 g of pure base. 1 g of this is dissolved in the minimum amount of ethanol, 0.33 g of fumaric acid is added, the mixture is stirred for 30 min at room temperature, the solvent is evaporated off under reduced temperature and the residue is recrystallized in isopropyl alcohol. 0.75 g of fumarate is finally isolated. Melting point: 159-160° C.

EXAMPLE 6

Compound No. 15

2-[{1-[(3-Methylphenyl)methyl]-4-piperidyl)methyl]-2,3,4,5-tetrahydro-1H-3-benzazepine difumarate 1 g (2.8 mmol) of 2-[{1-[(3-methylphenyl)carbonyl]-4-piperidyl)methyl]-2,3,4,5-tetrahydro-1H-3-benzazepine, dissolved in 50 ml of tetrahydrofuran, is added under an argon atmosphere to a suspension of 0.26 g (7 mmol) of lithium aluminium hydride in 10 ml of tetrahydrofuran. The mixture is stirred at 60° C. for 2 h, hydrolyzed by adding successively 1 ml of water and 2 ml of 1N sodium hydroxide, dried over magnesium sulphate and filtered, and the filtrate is evaporated under reduced pressure. 0.8 g of oily residue is obtained, and this is taken up with the minimum amount of ethanol, 0.55 g of fumaric acid dissolved in ethanol is added, and the white crystals which precipitate are filtered off. 0.5 g of difumarate is finally isolated. Melting point: 212°-213° C.

EXAMPLE 7

Compound No. 20

2-[{1-[(3-Methylphenyl)carbonyl]-4-piperidyl}methyl]-2,3,4,5-tetrahydro-1H-2-benzazepine hydrochloride 3 g (0.02 mol) of 2,3,4,5-tetrahydro-1H-2-benzazepine, 7.6 g (0.02 mol) of (1-[(3-methylphenyl)carbonyl]-4-piperidyl)methyl 4-methylbenzenesulphonate, 2.8 g (0.02 mol) of potassium carbonate and 20 ml of dimethylformamide are introduced into a round-bottomed flask placed under argon and equipped with a stirring system. The mixture is stirred for 9 h at 90° C., cooled and poured into water. The mixture is extracted with dichloromethane, the organic phase is washed with water and dried over magnesium sulphate and the solvents are evaporated off under reduced pressure. 6.5 g of residue are obtained, and this is purified by chromatography on a silica column, eluting with ether, yielding 2.5 g of pure base. 1 g of this is dissolved in the minimum amount of ethanol, 28 ml of a 0.1N solution of hydrochloric acid in 2-propanol are added, the mixture is stirred for 30 min at room temperature, the solvents are evaporated off under reduced pressure and the residue is recrystallized in isopropyl alcohol. 0.6 g of hydrochloride isolated. Melting point: 192°-193° C.

EXAMPLE 8

Compound No. 21

2-[{1-[(3-Methylphenyl)methyl]-4-piperidyl}methyl]-2,3,4,5-tetrahydro-1H-2-benzazepine difumarate 1.5 g (4.1 mmol) of 2-[{1-[(3-methylphenyl)carbonyl]-4-piperidyl)methyl]-2,3,4,5-tetrahydro-1H-2-benzazepine, dissolved in 20 ml of tetrahydrofuran, are added under an argon atmosphere to a suspension of 0.314 g (8.2 mmol) of lithium aluminium hydride in 20 ml of tetrahydrofuran. The mixture is stirred at 60° C. for 2 h, hydrolyzed by adding successively 1 ml of water and 2 ml of 1N sodium hydroxide, dried over magnesium sulphate and filtered, and the filtrate is evaporated under reduced pressure 1.1 g of oily residue are obtained, and this is taken up with the minimum amount of ethanol, 0.67 g of fumaric acid dissolved in ethanol is added, and the white crystals which precipitate are filtered off. 1.2 g of difumarate are finally isolated. Melting point: 176°–177° C.

The table below illustrates the chemical structures and physical properties of a few compounds according to the invention. In the "salt" column, "HCl" denotes the hydrochloride, "diHCl" denotes the dihydrochloride, "fum." denotes the fumarate and "difum." denotes the difumarate. The asterisk* denotes a dihydrated salt.

TABLE

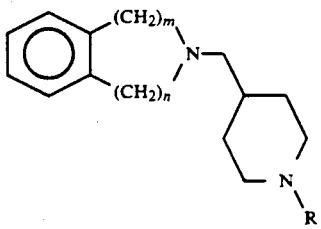

| No | m | n | R | Salt | M.p. (°C.) |
|----|---|---|---|------|------------|
| 1  | 1 | 1 | H | diHCl | 298–301 |
| 2  | 1 | 1 | $C_6H_5$—CO— | HCl | 225–227 |
| 3  | 1 | 1 | $C_6H_5$—$CH_2$— | diHCl | 291–293 |
| 4  | 1 | 1 | 3-Cl—$C_6H_4$—CO— | fum. | 141–143 |
| 5  | 1 | 1 | 3-Cl—$C_6H_4$—$CH_2$— | difum. | 198.5–200.5 |
| 6  | 1 | 1 | 3-$CH_3$—$C_6H_4$—CO— | HCl | 217.5–220 |
| 7  | 1 | 1 | 3-$CH_3$—$C_6H_4$—$CH_2$— | difum. | 198–200.5 |
| 8  | 1 | 1 | 3-$C_2H_5O$—$C_6H_4$—$CH_2$— | HCl | 171–173 |
| 9  | 1 | 1 | 3-$C_2H_5O$—$C_6H_4$—$CH_2$— | difum. | 206.5–208 |
| 10 | 2 | 2 | $C_6H_5$—CO— | fum. | 210–212 |
| 11 | 2 | 2 | $C_6H_5$—$CH_2$— | difum. | 220–222 |
| 12 | 2 | 2 | 3-Cl—$C_6H_4$—CO— | fum. | 197–198 |
| 13 | 2 | 2 | 3-Cl—$C_6H_4$—$CH_2$— | difum. | 189–190 |
| 14 | 2 | 2 | 3-$CH_3$—$C_6H_4$—CO— | fum. | 159–160 |
| 15 | 2 | 2 | 3-$CH_3$—$C_6H_4$—$CH_2$— | difum. | 212–213 |
| 16 | 3 | 1 | $C_6H_5$—CO— | HCl | 226–227 |
| 17 | 3 | 1 | $C_6H_5$—$CH_2$— | difum. | 179–180 |
| 18 | 3 | 1 | 3-Cl—$C_6H_4$—CO— | HCl | 182–185 |
| 19 | 3 | 1 | 3-Cl—$C_6H_4$—$CH_2$— | difum. | 178–180 |
| 20 | 3 | 1 | 3-$CH_3$—$C_6H_4$—CO— | HCl | 192–193 |
| 21 | 3 | 1 | 3-$CH_3$—$C_6H_4$—$CH_2$— | difum. | 176–177 |
| 22 | 3 | 1 | 3-$C_2H_5O$—$C_6H_4$—CO— | HCl | 170–173 |
| 23 | 3 | 1 | 3-$C_2H_5O$—$C_6H_4$—$CH_2$— | diHCl* | 210–214 |

The compounds of the invention were subjected to a series of pharmacological tests which demonstrated their value as substances having therapeutic activity.

Thus, they were subjected to a study in respect of their affinity for 5-HT$_1$A type serotoninergic receptors.

In the rat hippocampus, the compounds displace the binding to these receptors of a labelled specified ligand, [$^3$H]-8-hydroxy-2-dipropylaminotetralin (hereinafter designated "[$^3$H]-8-OH-DPAT"), described by Gozlan et al., Nature, (1983), 305, 140–142.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion for 10 min at 48,000×g and resuspending the pellet in cooled fresh buffer. Finally, the last pellet is suspended in the buffer to produce a concentration of 100 mg of original tissue per ml of 50 mM buffer.

The suspension is then left to incubate at 37° C. for 10 min.

The binding with [$^3$H]-8-OH-DPAT (1 nM) is determined by incubating 100 μl of membrane suspension in a final volume of 1 ml of buffer containing 10 μM pargyline and 3 μM paroxetine.

After an incubation for 5 min at 37° C., the membranes are recovered by filtration on Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OH-DPAT is defined as the amount of radioactivity retained on the filters and capable of being inhibited by coincubation in 10 μM 5-hydroxytryptamine. At a [$^3$H]-8-OH-DPAT concentration of 1 nM, the specific binding represents from 70 to 80% of the total radioactivity recovered on the filter.

For each concentration of test compounds, the percentage inhibition of the binding with [$^3$H]-8-OH-DPAT and then the IC$_5$0 concentration, the concentration which inhibits 50% of the binding, are determined.

For the compounds of the invention, the IC$_5$0 values lie from 0.001 to 1 μM.

Another in vitro test showed, moreover, that the compounds according to the invention have an affinity with respect to the σ (sigma) receptors of the membranes of the rat cerebral cortex, which marks them out as potential antipsychotic agents.

The central activity of compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358–361 (Karger, Basel 1977).

Cumulative doses of test compounds are administered (from 0.001 to 3 mg/kg intravenously) at 30-min time intervals, 4 h after the intraperitoneal injection of a dose of 0.75 mg/kg of reserpine, to curarized cats under artificial ventilation. The electroencephalographic and phasic (PGO-R spike) activities are obtained using cortical and deep (lateral geniculate) electrodes. For each dose of test compound, the percentage decrease in the number of PGO spikes and then the AD$_5$0, the active dose which decreases this number of spikes by 50%, are determined.

For the compounds of the invention, the intravenous ED$_5$0 values lie from 0.003 to 3 mg/kg.

The results of the tests show that the, compounds of the invention possess, in vitro, a high affinity and a selectivity for 5-HT$_1$A type serotoninergic receptors, as well as for sigma type receptors. In vivo, they show an agonist or partial agonist activity with respect to these receptors.

The compounds of the invention may hence be used for the treatment of diseases and conditions directly or indirectly involving the 5-HT$_1$A and/or sigma type serotoninergic receptors, in particular for the treatment of depressive states, anxiety states, psychotic states such as schizophrenia and sleep disorders, and for the regulation of food intake, and also for the treatment of vascular, cardiovascular and cerebrovascular disorders such as hypertension or migraine.

The present invention also provides a derivative or composition as defined above for use in a method of treatment of the human or animal body by therapy, in particular for use in a method of treatment of a depressive state, anxiety state, psychotic state or vascular, cardiovascular or cerebrovascular disorder or for the regulation of food intake.

The present invention further provides the use of a derivative as defined above in the manufacture of a medicament for the treatment of a depressive state, anxiety state, psychotic state or vascular, cardiovascular or cerebrovascular disorder or for the regulation of food intake.

For this purpose, the compounds of the invention may be presented in all forms suitable for their oral or parenteral administration, in combination with all suitable excipients and in doses permitting a daily dosage of, for example, 1 to 1000 mg. Accordingly the present invention also provides a pharmaceutical composition which comprises a derivative as defined above and a pharmaceutically acceptable excipient.

We claim:

1. A benzazepine derivative that has formula (I):

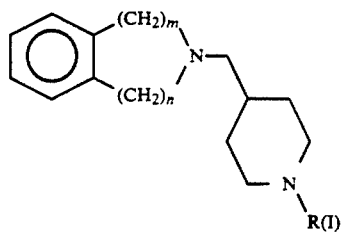

or a pharmacologically acceptable addition salt of the benzazepine derivative of formula (I), wherein:

m and n are each 2 and R is —CO—R', or m is 3 and n is 1 and R is —CO—R' or —CH$_2$—R'; and R' is a phenyl group which unsubstituted or is substituted with from one to three substituents selected form th group consisting of halogen atoms, linear or branched (C$_1$-C$_3$) alkyl groups and linear or branched (C$_1$-C$_3$) alkoxy groups.

2. A derivative according to claim 1, in which R' is a phenyl group substituted in the 3-position.

3. A derivative according to claim 1, in which R' is a phenyl group substituted with from one to three substituents selected from chlorine atoms, methyl groups and ethoxy groups.

4. A derivative according to claim 1, which is in the form of a dihydrochloride, hydrochloride, difumarate or fumarate salt.

5. A pharmaceutical composition for treatment of depressive or anxiety disorders, comprising a pharmaceutically effective concentration of a derivative of claim 1 and a pharmaceutically acceptable excipient, wherein said concentration is effective for ameliorating the symptoms of said disorders.

6. A method of treatment of depressive or anxiety disorders, comprising administering to a subject in need of or liable to be in need of such treatment an effective amount of the composition of claim 5.

* * * * *